United States Patent
Durack

(10) Patent No.: US 8,569,069 B2
(45) Date of Patent: Oct. 29, 2013

(54) SYSTEM AND METHOD FOR HIGH THROUGHPUT CELL ANALYSIS AND SORTING

(75) Inventor: Gary P. Durack, Urbana, IL (US)

(73) Assignee: Sony Corporation, Tokyo (JP)

( * ) Notice: Subject to any disclaimer, the term of this patent is extended or adjusted under 35 U.S.C. 154(b) by 175 days.

(21) Appl. No.: 13/089,806

(22) Filed: Apr. 19, 2011

(65) Prior Publication Data

US 2012/0094324 A1 Apr. 19, 2012

Related U.S. Application Data

(60) Provisional application No. 61/325,521, filed on Apr. 19, 2010.

(51) Int. Cl.
*G01N 33/48* (2006.01)
*C12Q 1/04* (2006.01)
*C12M 1/34* (2006.01)

(52) U.S. Cl.
USPC ............. 436/63; 436/164; 435/29; 435/34; 435/287.1; 435/288.4; 435/288.7; 422/73; 422/552

(58) Field of Classification Search
USPC ........ 436/63, 164, 165, 172, 174, 180; 435/4, 435/29, 34, 287.1, 288.2, 288.4, 288.5, 435/288.7; 422/407, 68.1, 73, 82.05, 82.08, 422/82.09, 502, 503, 547, 551, 552, 559
See application file for complete search history.

(56) References Cited

U.S. PATENT DOCUMENTS

| | | | |
|---|---|---|---|
| 7,229,838 B2 * | 6/2007 | Foster et al. | 436/180 |
| 2004/0166555 A1 * | 8/2004 | Braff et al. | 435/29 |
| 2007/0117086 A1 * | 5/2007 | Evans et al. | 435/4 |
| 2009/0258383 A1 * | 10/2009 | Kovac et al. | 435/29 |

OTHER PUBLICATIONS

Kovac et al. Analytical Chemistry, vol. 79, 2007, pp. 9321-9330.*

* cited by examiner

*Primary Examiner* — Maureen Wallenhorst
(74) *Attorney, Agent, or Firm* — Ice Miller LLP

(57) ABSTRACT

A sorting methodology in which bulk analysis of samples that have a low probability of containing a rare particle is performed first. Only those samples in which the bulk analysis has detected one or more rare particles are subjected to a flow cytometry process to isolate the rare particle(s). In one embodiment, a microwell plate provides for high throughput sorting in an enclosed environment. The microwell plate includes a plurality of wells and a microfluidic layer adapted for flow cytometry wherein particles from a given well are interrogated and sorted into other wells. The microfluidic layer advantageously includes fluid switches to permit bi-directional flow cytometry.

12 Claims, 3 Drawing Sheets

SYSTEM AND METHOD FOR HIGH THROUGHPUT CELL ANALYSIS AND SORTING

CROSS-REFERENCE TO RELATED APPLICATIONS

This application claims the benefit of the filing date of U.S. Provisional Application No. 61/325,521, filed Apr. 19, 2010, which is hereby incorporated by reference in its entirety.

TECHNICAL FIELD OF THE INVENTION

The present disclosure generally relates to fluid handling and, more particularly, to a system and method for high throughput cell analysis and sorting.

BACKGROUND OF THE INVENTION

High speed cell sorting has been an important research technology for many years. Examples of the many applications include isolation of rare populations of immune system cells for AIDS research, isolation of genetically atypical cells for cancer research, isolation of specific chromosomes for genetic studies, and isolation of various species of microorganisms for environmental studies.

Recently, two areas of interest are moving cell sorting towards clinical, patient care applications. First, is the move away from chemical pharmaceutical development to biopharmaceuticals. The majority of new cancer therapies are developed using biotechnology. These include a class of antibody-based cancer therapeutics. Cell sorters can play a vital role in the identification, development, purification and ultimately the production of these products. Related to this is a move toward the use of cell replacement therapy for patient care. Much of the interest in stem cells revolves around a new area of medicine often referred to as regenerative therapy or regenerative medicine. These therapies may often require that large numbers of relatively rare cells be isolated from patient tissue. For example, adult stem cells may be isolated from bone marrow and ultimately used as part of a re-infusion back into the patient from whom they were removed.

High speed cell sorters have typically utilized an electrostatic droplet technology similar to that used in early ink jet printers. This method is very efficient, allowing as many as 90,000 cells to be sorted per second from a single stream. This method is not, however, particularly biosafe. Aerosols generated in the droplet formation process can carry biohazardous material. Even though "biosafe" droplet cell sorters mounted in a biosafety cabinet are commercially available, even this type of system does not lend itself to the sterility and operator protection required for routine sorting of patient samples in a clinical environment. Microfluidics technologies offer great promise for providing cell sorting capability within a closed environment. Many microfluidic systems have been demonstrated that can successfully sort cells. They have the advantage of being completely self-contained, easy to sterilize, and can be manufactured in sufficient quantities to be a disposable part. These technologies have not been widely adopted largely due to cost considerations related to the maximum throughput achievable on such a device. The fastest of these devices operate at rates of 1000-2000 cells per second, nearly ten times slower than a droplet cell sorting system. One of the speed limitations of microfluidic devices is the ability to sort desirable cells from the remaining cells quickly. All of the cells move together in a stream of fluid, and the desired cells must be routed into a collection vessel while the remaining cells are routed into a waste vessel. The present disclosure relates to a high speed means for achieving such sorting, and can be implemented in a microfluidic device incorporated into a microwell plate.

SUMMARY OF THE INVENTION

A sorting methodology in which bulk analysis of samples that have a low probability of containing a rare particle is performed first. Only those samples in which the bulk analysis has detected one or more rare particles are subjected to a flow cytometry process to isolate the rare particle(s). In one embodiment, a microwell plate provides for high throughput sorting in an enclosed environment. The microwell plate comprises a plurality of wells and a microfluidic layer adapted for flow cytometry wherein particles from a given well are interrogated and sorted into other wells. The microfluidic layer advantageously includes fluid switches to permit bi-directional flow cytometry.

In a first embodiment of the invention, a microwell plate comprises a plurality of wells and a microfluidic layer adapted for flow cytometry, wherein particles from a given well are interrogated and sorted into other wells.

In a second embodiment of the invention, a method sorting particles comprises the steps of: (a) providing a microwell plate having a plurality of wells; (b) assigning to a subset of the wells batches of particles to be interrogated, wherein the probability of a given batch containing a desired target particle is substantially less than 1; (c) performing bulk interrogation of the batches within the subset of wells to identify batches that contain at least one target particle; and (d) performing flow cytometry to sort the desired target particles from the batches identified in step (c).

In a third embodiment of the invention, a method sorting particles comprises the steps of: (a) providing a plurality of batches of particles to be interrogated; (b) performing bulk interrogation of the batches to identify batches that contain at least one target particle; and (c) performing flow cytometry to sort the desired target particles from the batches identified in step (b).

DETAILED DESCRIPTION OF VARIOUS EMBODIMENTS

Figure 1A:
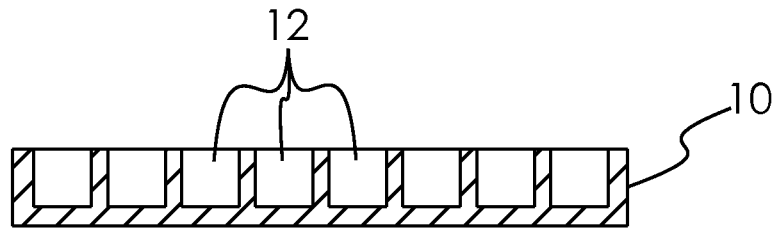
FIG. 1a is a diagram of an end view of a typical microwell plate.

For the purposes of promoting an understanding of the principles of the invention, reference will now be made to embodiments illustrated in the drawings, and specific language will be used to describe them. It will nevertheless be understood that no limitation of the scope of the invention is thereby intended. Alterations and modifications in the illustrated device, and further applications of the principles of the invention as illustrated therein, as would normally occur to one skilled in the art to which the invention relates, are contemplated.

The various embodiments described below provide a means for greatly increasing the speed and efficiency of sorting rare cells. They provide a novel cell analysis and sorting system that can provide very high throughput, especially for the detection and isolation of rare cell populations (e.g. <1% of the total cell suspension). This advantage can help render existing treatments more economical, help make feasible treatments that are presently impractical, or only theoretical or experimental, and improve the speed and reduce the cost of research of both the science and applications of molecular biology. To name just one example, the high speed cell sorting provided by the present invention can be used in the collection and isolation of adult stem cells.

Those skilled in the art will appreciate that microwell plates are routinely used in life science research for cell culture and as a container to support high-throughput assays. Many companies have developed fluorescence-based immuno-assays, which are often performed using such plates. In such assays, the sample in a well of the microwell plate is exposed to a fluorescenated reagent. A fluorescence plate reader is used to measure the total, average, and/or peak fluorescence emission from a well of the plate. These assays have been in use for many years. Substantial technology and automation has been developed to fill, empty and mix suspensions of cells in microwells. Likewise, substantial technology and automation has been developed to produce low cost plates that have high quality, flat, optical surfaces on the bottom to allow optical measurements to be made in the plate, and to manage the transport of plates in and out of processing areas, like cell culture incubators or biosafety cabinets, and to precisely position specific wells in plates in three dimensions over optics that can be used for image measurement of cells adherent to the bottom of the plate, or measurement of emissions from cells in suspension in the fluid in a well. Microwell plates are the standard tool for handling and processing of cells, sub-cellular components and their molecular components. Such plates are routinely delivered as sterile, disposable components to the laboratory.

Figure 1B:
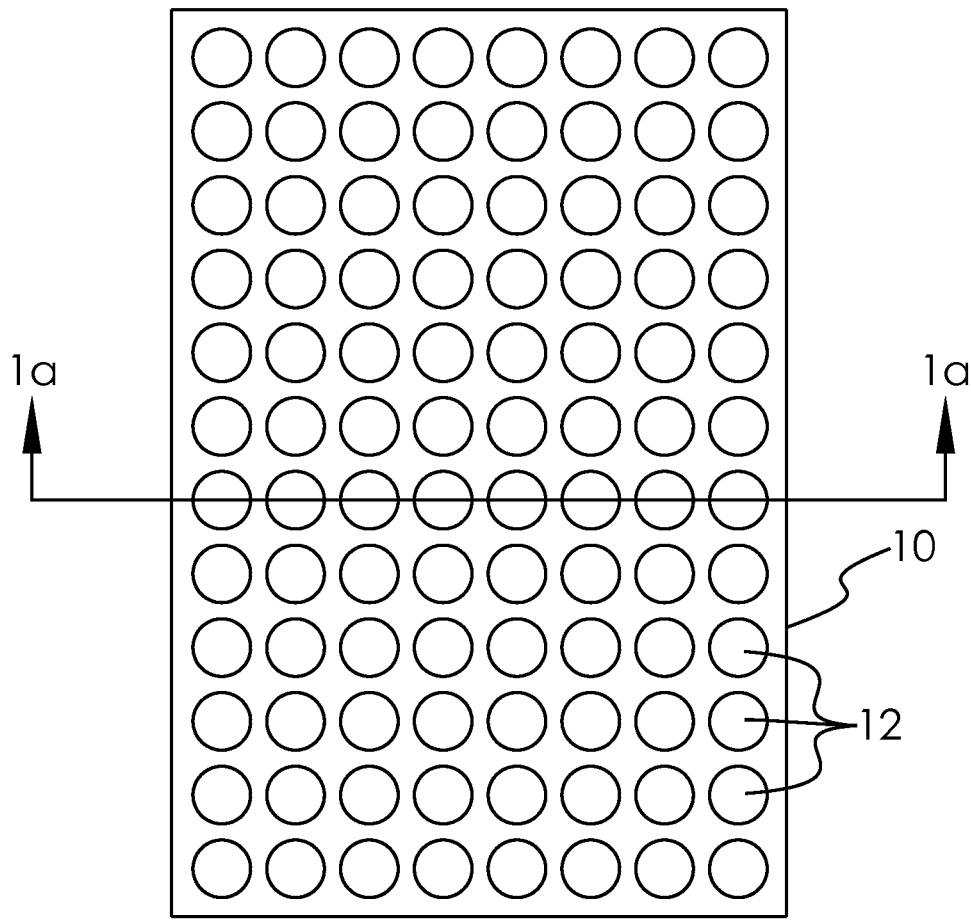
FIG. 1b is a diagram of a plan view of a typical microwell plate.

An innovation of this system is the use of microfludics to transport cells (or other particles) from one well of a microwell (microtiter) plate to another well of a microwell plate. FIGS. 1a and 1b show the end and top (or bottom) view, respectively, of microwell plate 10, having 96 wells 12. Plates 10 can have more or less wells 12 (e.g. 384 well plates and 24 well plates, to name just two non-limiting examples).

Figure 2:
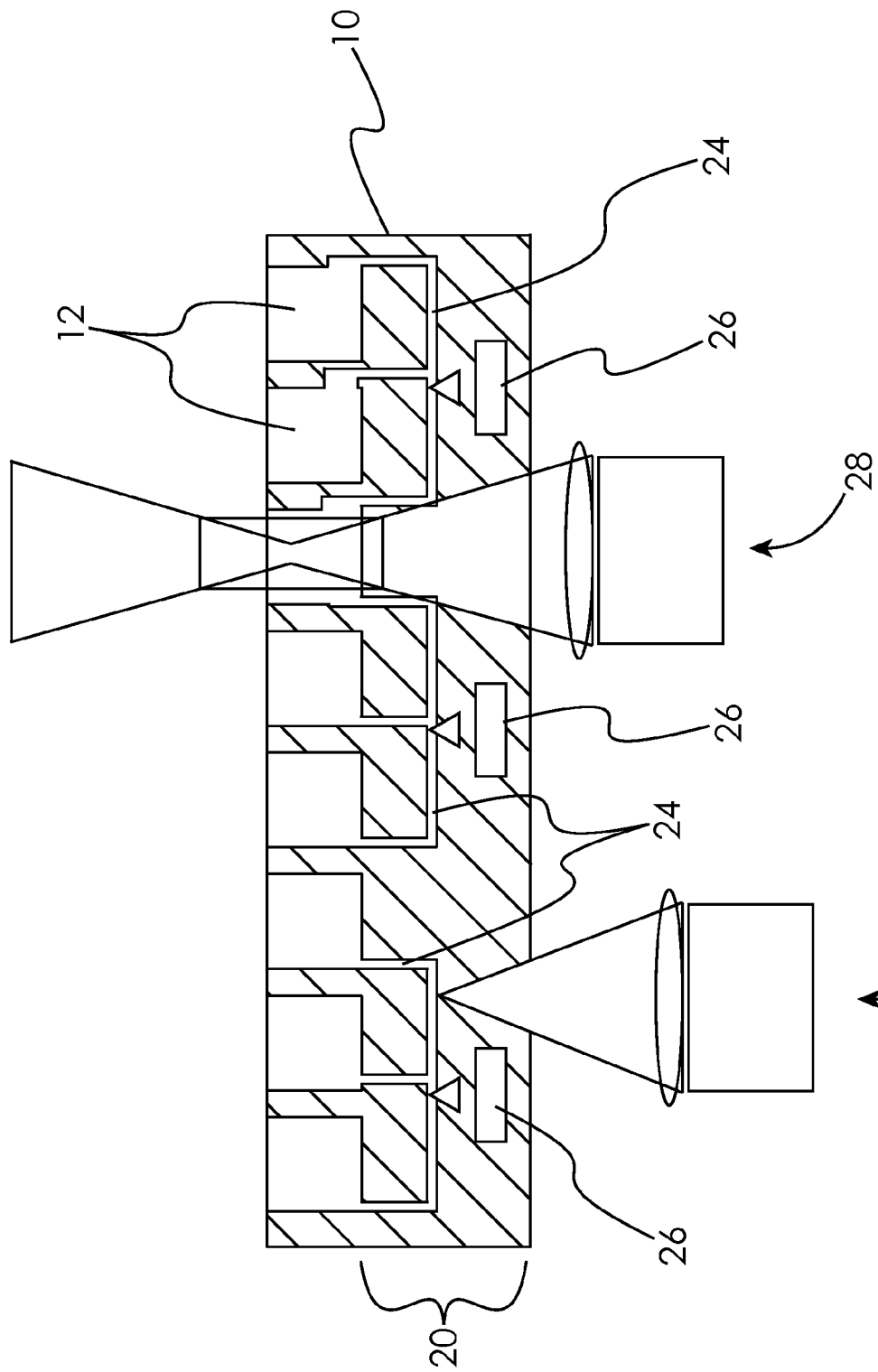
FIG. 2 is a diagram of an end view of certain microwell plates, illustrating the loci of bulk interrogation and single cell interrogation.

The presently disclosed embodiments utilize a custom, disposable microwell plate 10 that has a layer containing microfluidic devices integrated or bonded to the base of the plate. Such a design is illustrated in FIG. 2. Contained in the microfluidic layer 20 are channels 24 that can provide a path between wells 12 and fluid switches 26 that can route the flow of fluid, as well as the valves and other microfluidic elements required so that the cells suspended in the fluid in each of a set of the wells can be transported to other wells in a microfluidic cytometry process. The method of fluid transport can be by active pressure (positive or negative) placed on the source or destination well, or osmotic pumping, or any other suitable method. Any of the commonly used methods of motivating fluid flow through microfluidic channels may be used. It will be appreciated that the particular method of inducing flow is immaterial to the invention. The microfluidic layer 20 is preferably transparent and of sufficient optical quality to allow both bulk fluorescence measurement of the cells in suspension in a microwell (as shown schematically at 28) and a flow cytometry measurement of cells travelling through a channel 24 (as shown schematically at 29).

The microwell plate 10 can be used to achieve exceptionally high throughput, especially in the sorting of rare cells, through a combination of bulk fluorescence measurement and flow cytometry. Rare cells can be specifically labeled with a fluorescent reagent (or other detection method) such that a bulk measurement of an individual well will indicate whether at least one rare cell is present in a given well. For example, a single well could reasonably contain up to 300,000 cells in a 250 μl sample. When sorting for cells that are rarer than about 1 in 300,000, the bulk fluorescence measurement can be used to eliminate batches of cells approximately 300,000 at a time. When a batch of 300,000 or so cells is determined to have at least one of the rare cells within it, the contents of that well can then be sorted using the flow cytometry layer 20.

In the flow cytometry process of certain embodiments, cells from the sample wells pass through the focus of an epi-illumination optic where they interact with one or more laser beams of specific wavelengths in a manner typical for flow cytometry. Specifically in this case, flow is not a coaxial sheath flow, but a flow of cells through the channel. It is desirable, but not required, to produce a single-file stream of cells using elements of the microfluidic channel to focus the flow of the cells. Other techniques, such as acoustic forces, could be used as well. Measurements such as narrow angle light scatter, wide angle light scatter, electronic cell volume, and total fluorescence emission at specific wavelengths can be measured in a manner that is typical for flow cytometry. A fluid switch or valve can be used to switch the flow, and therefore the interrogated cell, into channels leading to one or more specific microwells. For example, the interrogated cell may be switched into a channel leading to a microwell for storing the desired rare cells, while the remainder of the flow can be routed to one or more channels leading to microwells for storing waste (or non-selected cells). Alternatively, the waste flow can be made to exit the plate 10. In this way the cells are sorted into specific microwells where they can be stored for further use or experimentation. The single cell measurement and sorting enables very high purity sorting of cells, even if they have very low incidence in the original cell suspension.

Besides the active switching technique described, other techniques can be used to motivate the cells into a specific destination well. These include electromagnetic separation where magnetic particles are bound to cells, electromagnetic actuation of a switching or microfluidic valve element, steering by acoustic forces, or steering by optical forces, just to name a few non-limiting examples. Any of a number of technologies known in the art can be used to steer the cell to the desired destination well.

It will be appreciated that any suitable methods of bulk interrogation and single cell flow cytometry may be used. For example, the laser illumination and emission detection from the single cell can, in many applications, be replaced by other methods of optical interrogation, magnetic interrogation, etc. As long as the technique provides adequately high specificity and sufficiently high signal to noise, the specific means for bulk and single cell interrogation are immaterial to the invention.

An advantage of the presently disclosed embodiments is that by coupling the bulk identification of wells containing rare cells with the microfluidic cell sorting, a very high effective cell sorting rate can be achieved while using a relatively slow fluid switching element.

For example, if a desired cell type exists in about 1 in 1,000,000 cells, 32 wells of a 96 well plate could be filled with samples of about 300,000 cells each. Statistically, 6-9 of these wells would be expected to have at least one of these cells within it. The bulk detection technique therefore rapidly excludes 72-81% of the cells from the next step, single cell sorting. The bulk measurement can be used to identify wells that lack rare target cells, so that the samples in those wells need not be individually sorted using the microfluidic channels.

Figure 3:
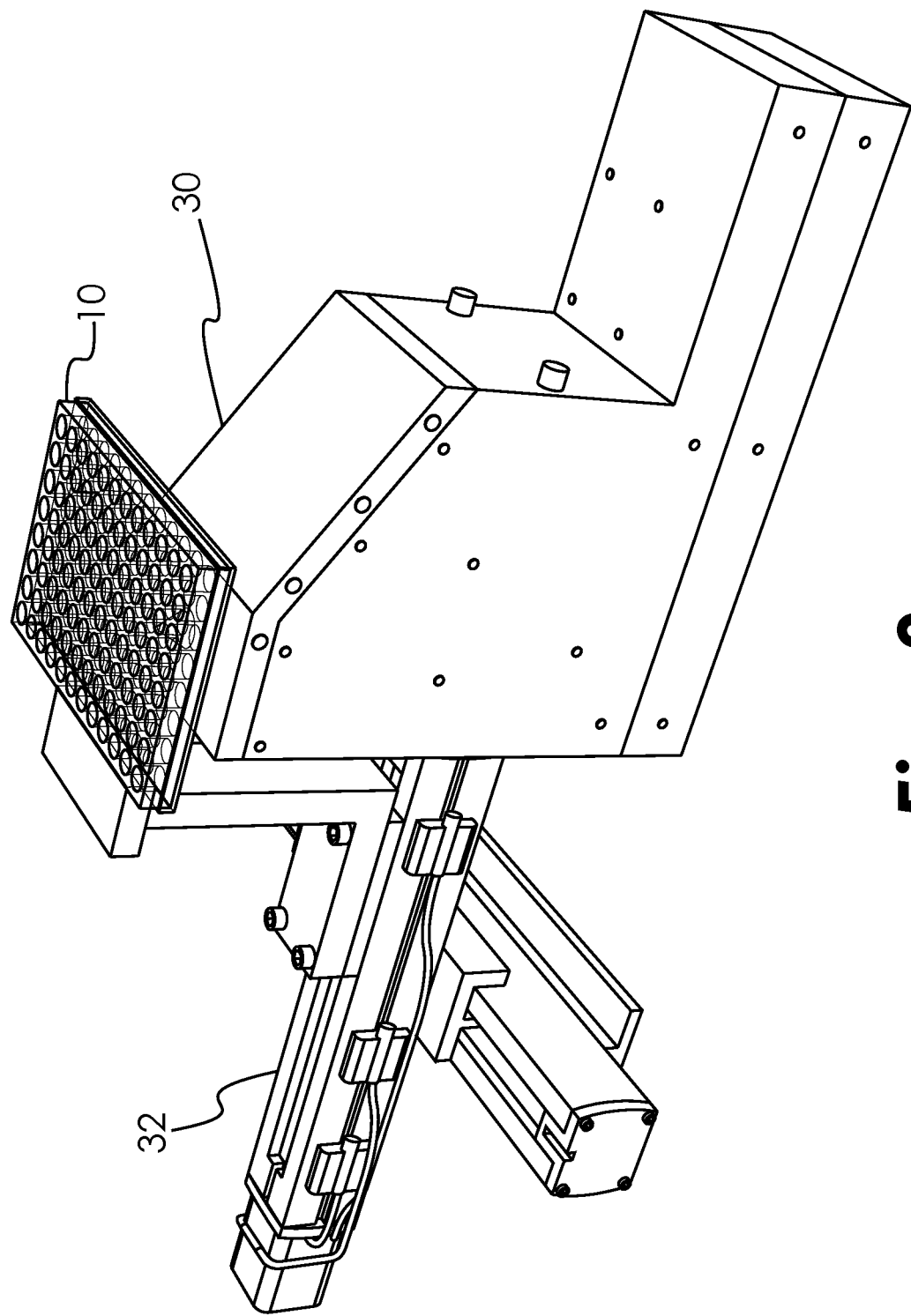
FIG. 3 is a perspective drawing of a microwell plate positioned on a plate cytometer with an X-Y stage for automatically repositioning the microwell plate for interrogation of different wells.

A typical layout for such a system is shown in FIG. 3. A microwell plate 10 is positioned on a long working distance epi-illumination optical system 30. The microwell plate 10 rests on a precision X-Y stage 32 that has sufficient resolution to place wells in position over the optic for bulk cell measurement or to align the optic's focus to a microfluidic channel for single cell measurement. A suitable optic is the Reflection Collection Optic typically used on the Reflection™ Cell Sorter available from iCyt Mission Technology, Inc., of Champaign, Ill. This optic consists of an off-axis elliptical mirror that has a large field of view (greater than 4 mm diameter), a long working distance (greater than 25 mm), and a high numerical aperture (0.84). This optic is well suited for this application, but it will be appreciated that other optics can also be used. Higher measurement and sorting throughput can be obtained by providing parallel detection and sorting components. A standard 96 well plate consists of an array of 8×12 wells. Therefore an 8 channel or 12 channel parallel system is a logical implementation.

To appreciate the high throughput of cell sorting provided by the presently disclosed embodiments, consider an example in which a sample of 10 million cells contains 10 desired target cells. After labeling for bulk interrogation and assignment to 32 wells of a 96 well plate, an 8 channel measurement system is used. At 5 seconds per bulk interrogation, it takes only 20 seconds to screen all 32 sample wells (5 s per bank, times four banks) It will be appreciated that 5 seconds per bulk interrogation is a very conservative estimate and is limited by the mechanics of moving the plate. The actual measurement time needed is much less than 1 second. Five seconds is used in this example to be conservative about a device that can easily be realized with the robotics commonly found in most labs today.

If the microfluidic flow cytometry process can sort at 1 KHz (a very modest rate), then the 300,000 or so cells in each well can be processed in 5 minutes (300,000 cells÷1000 cells/s). Statistical analysis reveals that is likely that the 10 target cells are contained in 8 or fewer wells. Assuming the samples in these wells are transferred to a bank of 8 wells for simultaneous single cell sorting, it will take on the order of 6 minutes to isolate 10 rare cells from 10,000,000. This cell sorting time is about what a traditional droplet cell sorter, operating at 30,000 cells per second, would require (10,000,000 cells/30,000 cells/s=333 s) for the same task. Even should the 10 target cells be distributed into 9 or 10 wells, requiring two runs of single cell sorting, the 10 cells can be isolated from a sample of 10,000,000 in on the order of 11 minutes. Since these times are dominated by the flow cytometry, increasing the microfluidic process to 2 KHz—a very feasible rate—cuts them nearly in half.

So the presently described sorting provides comparable speed to sorting at a rate of 30,000 cells per second with a traditional droplet cell sorter (which will actually be generating droplets at 90 KHz or less), and avoids the problems of the traditional droplet sorting, such as droplet coincidence (which causes either a loss of efficiency, i.e. losing the target cell, or a loss of purity, i.e. sorting an unwanted cell with the target cell) and actually finding the 10 sorted drops with the desired cells. To achieve the 30,000 cells per second rate it is necessary to place the fluid containing the cells under substantial pressure and jet them through the nozzle. This can be damaging to cells. Also if the desire is to sort large cells, or fragile cells, then the nozzle diameter must be increased on a traditional cell sorter. Increasing the nozzle diameter decreases the achievable droplet generation frequency. This will further reduce sorting efficiency as droplets are bigger and cell coincidence in them rises. In traditional droplet sorting, locating the sorted cells in the container used to capture the deflected droplets, travelling at velocities on the order of 10-30 m/s, is a significant problem. The presently described sorting not only handles the cells much more gently, it places the cells in a small volume of fluid in a microwell plate, to be stored and later retrieved using nano or micro pipettes (or further analyzed in place).

It will be appreciated that, to optimize the efficiency of the sorting, it is desirable for the probability of a well to contain a rare cell to be significantly less than 1. In applications without a parallel detector array, when the probability is approximately 0.5, the speed of sorting an entire plate is, on average, nearly doubled, since the single cell interrogation typically dominates the process time. It is therefore desirable in some cases to limit the number of cells in the wells based on the expected rate of occurrence of the desired target cells among the sample population. For example, if the desired target cells make up about 0.01% of the sample population, then the probability of a well containing at least one target cell is about 0.5 when the number of cells is about 7000. In general, the probability, $P_n$, that a well contains at least one target cell is given by:

$$P_n = 1-(1-K)^n \qquad (1)$$

where K is the fraction of the supply population that constitute the desired target cells, and n is number of cells per well. Solving for n, in the case where K=0.01%, therefore, it will be appreciated that to cause about half of the wells to contain at least one desired target cell:

$$0.5 = 1-(1-0.0001)^n \qquad (2)$$

$$\ln(0.5) = \ln(0.9999)^n \qquad (3)$$

$$\ln(0.5) = n \ln(0.9999) \qquad (4)$$

$$n = \ln(0.5)/\ln(0.9999) \approx -0.6931 \div -0.0001 \approx 6931 \qquad (5)$$

It will be appreciated that, depending on the ratio of the time required to perform the bulk searches to the time required to perform single cell sorting of the wells, the desired fraction of wells that should contain at least one target cell may vary. Generally, however, the time for single cell sorting will dominate, since, to the extent bulk sorting time becomes a meaningful contribution, it can be eliminated by performing single cell sorting for one set of wells and bulk sorting for the next simultaneously. Typically, therefore, $P_n \approx 0.5$ will tend to be optimal.

It will also be appreciated that, in embodiments in which parallel flow cytometry is employed, the time to perform single cell sorting for a given bank of wells is required whenever at least one of the wells in that bank contains at least one target cell. Consequently, in this case, n in the equations represents the number of cells per bank of wells that are interrogated and sorted in parallel, rather than the number of cells per individual well. However, as long as flow cytometry times dominate, when using parallel flow cytometry elements, it will generally be preferable to optimize sorting by transferring batches to fill an entire bank of wells under single cell interrogation, where each batch contains at least one target cell. To assist in doing so, the microfluidic layer can also include passages for transferring fluid between wells intended to serve as source wells.

Thus, in certain embodiments, bulk interrogation and single cell sorting occurs simultaneously, but in others they do not. For example, entire plates, or batches of plates, can undergo bulk sorting to identify wells for later flow cytometry. In fact, there is no need for the bulk and single cell interrogations to be performed by the same device. This might be particularly useful, for example, in contexts in which only one or two wells worth of desired cells are needed on each of several days. In some contexts, plates could be frozen, and the time between bulk and single cell sorting could be years.

High throughput sorting can also be achieved with a cyclical process using such a microwell plate. An automated cell delivery system could be used to load, for example, a bank of 8 wells at a time, into every 3rd row of wells (leaving the other wells for sorting). Bulk interrogation is used to identify wells containing target cells, and those found to contain them are sorted. Afterwards, the wells are emptied by an 8 channel pipette, and then reloaded with another batch of cells. This could include the waste receptacle wells, but leaving the wells containing the target cells, to accumulate with target cells from further rounds of sorting.

One advantage of the presently disclosed microwell plates is that the cell sorting takes place in a closed environment. One advantage of this is related to potential biohazard conditions. Microwell plates are often handled according to biohazard handling standards such as BSL2, BSL 4, etc. The presently disclosed embodiments are easily adaptable to accommodate these standards. Prior art droplet cell sorters, by contrast, can create significant aerosol hazard.

Another advantage of the closed environment provided by the presently disclosed embodiments is the potential reduction of waste and improved thoroughness in harvesting rare cells. In traditional cytometry applications, desired cells are lost to waste due to detection or sorting failures. Sorting on a microwell plate as described herein merely involves moving cells from one well to another. Fluid in the "waste" wells could even be re-run through bulk sorting, and, if desired cells are located, flow cytometry run again to capture the target cells that were missed the first time. Such bi-directional sorting and analysis could be used on separate occasions, separated, for example, by a period of incubation (possibly days). It could also be used, for example, to resort under different interrogation means, such as different fluorescence wavelengths, using different lasers, photodetectors, etc.

Likewise, the use of such microwell plates helps with processing and maintenance of live cells. The microwell plates can be stored under environmentally favorable conditions, such as a cell incubator, removed for cell processing (measurement and sorting), and returned to the controlled environment afterwards.

The microwell plates can also be pre-loaded and packaged with lyophilized reagents, or reagents stored in any manner compatible with long term storage. Sample preparation can be automated, taking place in the source wells. For example, wells can be pre-loaded with specific combinations of fluorescenated monoclonal antibodies. When cells are added to the well and mixed the labeling reaction will take place. The plate can, therefore, serve as the reagent delivery and sample preparation platform.

It will be appreciated that the fluid connections between the wells are not required to be in a separate layer below the wells as shown in the embodiment above. The connections between the various bulk wells could be done in any manner, including connecting the wells directly in the layer in which the wells reside. In fact, it is not necessary that the arrangement of the bulk measurement receptacles (or wells) in fact be a microwell plate. The presently disclosed embodiments recognize that a much higher processing rate and efficiency in cell sorting can be achieved by combining the benefits of single cell detection in bulk with the advantages of single cell sorting flow cytometry using microfluidics. Breaking up the overall sample into small suspensions such that the probability of the detection of a rare cell in an individual aliquot of the suspension is at most a few percent makes this possible. The embodiments disclosed herein using microwell plates are attractive because so much robotic and automated fluid and plate handling technology already exists.

One advantage of bonding or integrating the fluid flow and analysis channel layer to the base of the sample well layer is this places the measurement channels in a position that they can be used for the high numerical aperture measurement used in flow cytometry. A short working distance to the fluid channel is desirable to achieve the high numerical aperture light collection used in the flow cytometry portion of the measurement. However, those skilled in the art will recognize that other arrangements may also be used.

In some embodiments, the plate may be formed as a rotatable disk, like a digital versatile disk (DVD), with many micro wells located in it. The indexing time to move a desired sample well into position would be similar to what is required for addressing a specific location on a DVD. In such embodiments, technologies that currently exist for manufacturing DVDs and for moving read/write heads around the DVD surface find direct application to the arrangements and methodologies disclosed herein.

In rare event applications, the challenge often will be how to sufficiently concentrate the cell suspension for sorting. In some embodiments, the cells are actually grown in the plate sample wells in an incubator. The plate may be taken out of the incubator and the wells scanned for occurrence of the rare cells. Only the wells where rare cells have occurred are harvested and the plate is put back into the incubator to allow the other wells to continue to grow.

It will be further appreciated that the methodologies disclosed hereinabove may be run in reverse. For example, it may be desired to screen material to put back into a patient and we want to be sure that the material DOES NOT contain a rare cancer cell. In this case, the "waste product" becomes the sorted product (i.e. the cancer cells) and the remaining material may be safely put back into the patient. Other sorting situations will also benefit from this "reverse methodology."

For the purpose of this document, the term "particle" refers to anything that may be detected using a flow cytometry apparatus. The term "source" refers to any source of particles that are supplied to a flow cytometry apparatus, and a "source well" is any well that contains and supplies particles for flow cytometry. The term "flow cytometry" refers to a process in which particles are physically sorted from one another according to some predetermined criteria, and to distinguish from "cytometry," in which particles are merely observed in order to quantify different types of particles within a sample.

While the invention has been illustrated and described in detail in the drawings and foregoing description, the description is meant to be illustrative, and not restrictive in character. Only the preferred embodiments, and certain alternative embodiments deemed useful for further illuminating the preferred embodiments, have been shown and described. All changes and modifications that come within the spirit of the invention are desired to be protected.

What is claimed is:

1. A method sorting particles, comprising the steps of:
   (a) providing a microwell plate having a plurality of wells;

(b) introducing batches of particles into a subset of wells to be interrogated, wherein the probability of a given batch containing a desired target particle is substantially less than 1;

(c) performing bulk interrogation of the batches within the subset of wells to identify batches that contain at least one target particle;

(d) transferring the batches identified by the bulk interrogation of step (c) into banks of cytometry wells constructed and arranged for simultaneous flow cytometry; and (e) performing flow cytometry on the banks of cytometry wells in parallel to sort the desired target particles from the batches identified in step (c).

2. The method of claim 1, wherein the flow cytometry of step (e) is performed entirely within a closed environment within the microwell plate.

3. The method of claim 1, wherein the flow cytometry of step (e) sorts the particles by moving identified target particles into a first portion of the cytometry wells and other particles into a second portion of the cytometry wells.

4. The method of claim 3, further comprising the step of:
(f) performing flow cytometry on the contents of the first portion of the cytometry wells.

5. The method of claim 3, further comprising the step of:
(f) performing flow cytometry on the contents of the second portion of the cytometry wells.

6. A method sorting particles, comprising the steps of:
(a) providing a plurality of batches of particles to be interrogated;

(b) performing bulk interrogation of the batches to identify batches that contain at least one target particle;

(c) transferring the batches identified by the bulk interrogation of step (b) into banks of cytometry wells constructed and arranged for simultaneous flow cytometry; and (d) performing flow cytometry on the banks of cytometry wells in parallel to sort the desired target particles from the batches identified in step (b).

7. The method of claim 6, wherein the probability of a given batch containing a desired target particle is substantially less than 1.

8. The method of claim 6, wherein said plurality of batches are placed into a respective plurality of sample wells on a microwell plate.

9. The method of claim 8, wherein the flow cytometry of step (d) is performed entirely within a closed environment within the microwell plate.

10. The method of claim 8, wherein the flow cytometry of step (d) sorts the particles by moving identified target particles into a first portion of the cytometry wells and other particles into a second portion of the cytometry wells.

11. The method of claim 10, further comprising the step of:
(e) performing flow cytometry on the contents of the first portion of the cytometry wells.

12. The method of claim 10, further comprising the step of:
(e) performing flow cytometry on the contents of the second portion of the subset of the second portion of the cytometry wells.

* * * * *

UNITED STATES PATENT AND TRADEMARK OFFICE
CERTIFICATE OF CORRECTION

PATENT NO. : 8,569,069 B2
APPLICATION NO. : 13/089806
DATED : October 29, 2013
INVENTOR(S) : Gary P. Durack It is certified that error appears in the above-identified patent and that said Letters Patent is hereby corrected as shown below:

On the Title Page, item (73), Assignee should read:  Sony Corporation (Tokyo, JP)
Sony Corporation of America, (New York, NY)

Signed and Sealed this
Eighth Day of July, 2014

Michelle K. Lee
*Deputy Director of the United States Patent and Trademark Office*